United States Patent
Erdmann et al.

(10) Patent No.: US 6,998,482 B2
(45) Date of Patent: Feb. 14, 2006

(54) PROCESS FOR THE PREPARATION OF DIRECTLY COMPRESSIBLE α-MANNITOL

(75) Inventors: Martin Erdmann, Gross-Gerau (DE); Walter Hamm, Weiterstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/498,567

(22) PCT Filed: Dec. 13, 2002

(86) PCT No.: PCT/EP02/14202

§ 371 (c)(1),
(2), (4) Date: Jun. 14, 2004

(87) PCT Pub. No.: WO03/055834

PCT Pub. Date: Jul. 10, 2003

(65) Prior Publication Data

US 2005/0008693 A1    Jan. 13, 2005

(30) Foreign Application Priority Data

Dec. 13, 2001  (DE) .............................. 101 61 402

(51) Int. Cl.
*C07C 31/26* (2006.01)
*B01J 2/00* (2006.01)
(52) U.S. Cl. .................... 536/124; 536/123.1; 424/464; 424/489; 264/109

(58) Field of Classification Search ............. 536/123.1, 536/124; 424/464, 489; 264/109
See application file for complete search history.

(56) References Cited

U.S. PATENT DOCUMENTS 3,145,146 A * 8/1964 Lieberman et al. ......... 424/465
5,324,751 A    6/1994 DuRoss

FOREIGN PATENT DOCUMENTS

| EP | 0 380 219 | 8/1990 |
| JP | 61 085330 | 4/1986 |
| WO | WO 97/38960 | * 10/1997 |

OTHER PUBLICATIONS

Patent Abstracts of Japan, vol. 010, No. 258, Sep. 4, 1986.
Bauer H et al., "Investigations on Polymorphism of Mannitol/Sorbitol Mixtures after Spray-drying using Differential Scanning Calorimetry, X-ray Diffraction and Near-Infrared Spectroscopy", Pharmazeutisch Industrie, Bd. 62, Nr. 3, 2000.

* cited by examiner

Primary Examiner—James O. Wilson
Assistant Examiner—Ganapathy Krishnan
(74) Attorney, Agent, or Firm—Millen, White, Zelano & Branigan, P.C.

(57) ABSTRACT

The present invention relates to a process for the preparation of directly compressible mannitol having a content of the α modification of greater than 90%.

20 Claims, 1 Drawing Sheet

PROCESS FOR THE PREPARATION OF DIRECTLY COMPRESSIBLE α-MANNITOL

Figure 1:
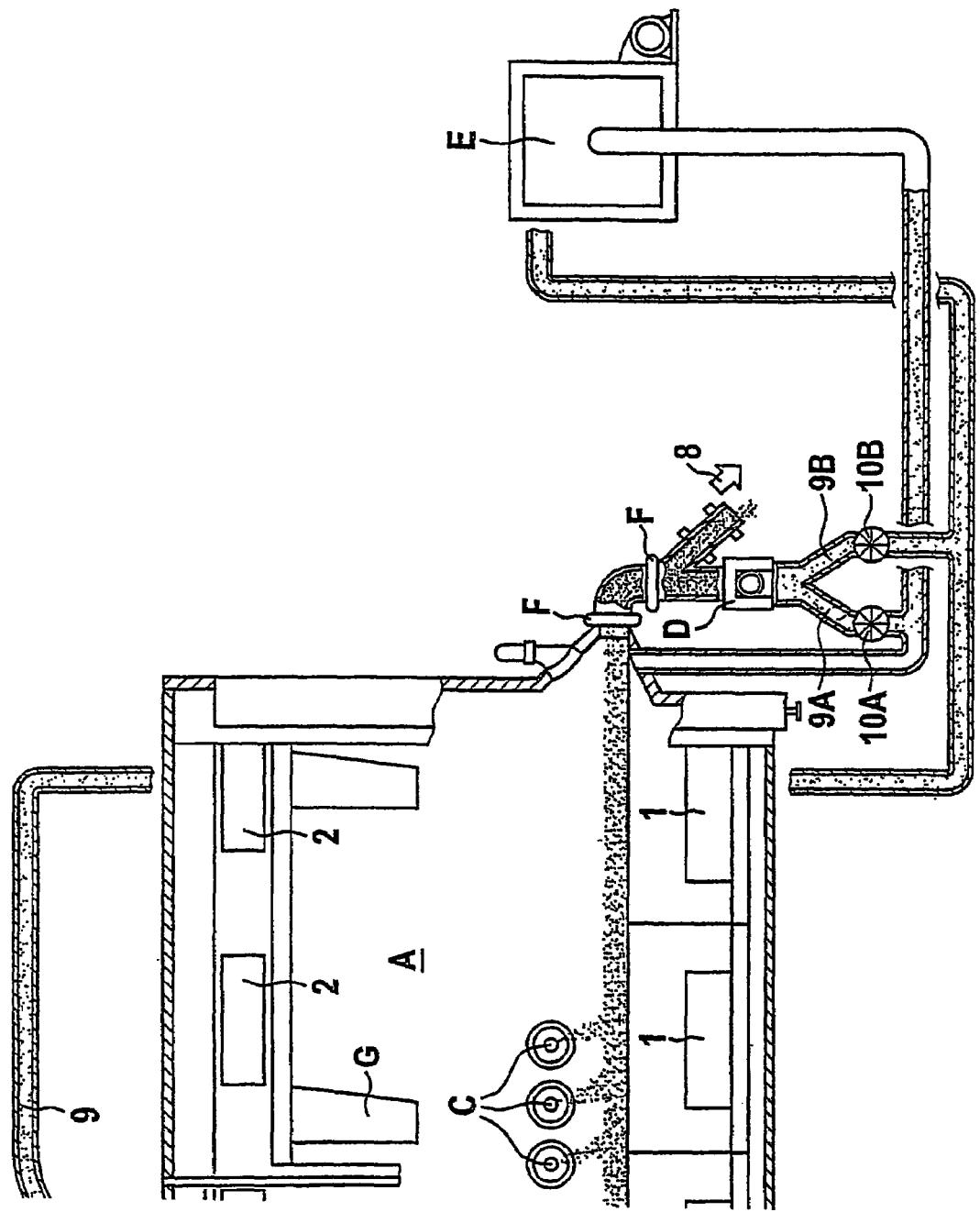

The present invention relates to a process for the preparation of directly compressible mannitol having a content of the α modification of greater than 90% by weight.

For the production of tablets, D-mannitol can be employed as excipient material for an active ingredient. To this end, the D-mannitol is usually converted into a pulverulent or granular form by a plurality of process steps with corresponding interim checks in order to enable it to be handled for tablet pressing and at the same time to facilitate binding-in of active ingredient.

U.S. Pat. No. 3,145,146 A discloses a spray-drying process by means of which mannitol is obtained in the form of fine particles having an average diameter of from 5 to 150 μm. A mannitol solution is spray-dried by atomisation into a stream of hot gas. The particles obtained are separated off by suitable measures. The process described gives a mixture of various crystal modifications.

It has also been disclosed that pulverulent D-mannitol can be prepared by granulation in a fluidised bed, in which the stream of process air flows through a specially shaped impingement plate, producing a fluidised bed from solid starting material. The spray liquid passes into the fluidisation space in finely divided form through a nozzle system. The fluidising particles are wetted, the surface is partially dissolved, and the particles adhere to one another. Solid is withdrawn continuously at the end of the fluidised bed. At the same time, a relatively small amount of solid, onto which spray liquid is finely distributed, is fed in at the inlet. A filter system prevents dust from leaving the fluidised bed, and only granule particles which have a minimum size are withdrawn at the exit. In addition, solid particles which have a more or less random shape form in a fluidised bed of this type. Corresponding plants are marketed by various manufacturers.

The preparation of pulverulent mannitol is usually followed by a process step by means of which a powder having a uniform particle size distribution is obtained. This process step can include both grinding and screening (classification) of the powder. In the case of the use of mannitol as excipient material for pharmaceutical active ingredients, any additional process step in the preparation represents to the person skilled in the art a possible risk of the introduction of undesired impurities into the product.

It is furthermore known from the literature that D-mannitol can exist in polymorphic crystal forms; these can be the α, β and δ forms. The definitions and characterisations used here correspond to the classification of polymorphic forms by X-ray structural analysis (X-ray diffraction pattern) given in Walter Levy, L.; Acad. Sc. Paris, t. 267 Series C, 1779 (1968). The β form is the most stable form, although conversions into the other forms are possible depending on the storage time and the ambient conditions. For commercial applications, it is therefore desirable per se to obtain mannitol in the β form, owing to its stability, since the product properties change to the least possible extent due to storage in this case.

It is furthermore known that on the one hand the polymorphic form in which the pulverulent D-mannitol exists and on the other hand the manner in which the particle structure of the individual particles has been built up are of importance for the compression properties of the pulverulent D-mannitol. This also has a crucial influence on the possibility of obtaining tablets in which the active ingredients present are homogeneously distributed.

WO 97/38960 A1 describes that improved compression properties arise through partial or complete conversion of the pulverulent D-mannitol from the δ form into the β form. Conversion from the δ form into the β form is caused by targeted wetting of the particle surfaces of the powder with a water-soluble solvent or water and by subsequent drying. The percentage of β-mannitol formed is dependent on the amount of solvent employed and the duration of the drying operation. A mixture of δ and β forms is therefore usually present in the product.

It is disadvantageous in this process that the conversion is an additional process step which follows the actual powder preparation, and the drying requires at least 8 hours, during which the plant has to be continuously supplied with thermal energy.

In contrast to the δ and β modification forms described, α-mannitol has hitherto principally been isolated from the melt. This process is labour- and energy-intensive. The product obtained in this way has poor compression properties.

The object of the present invention is therefore to provide a process for the preparation of directly compressible α-mannitol which can be carried out in a simple manner.

The object of the invention is also to provide a process by means of which, in a first step, directly compressible α-mannitol is prepared, which, in subsequent process steps, is incorporated into formulations comprising active ingredient and can be converted into β-mannitol in a simple manner for homogeneous and stable binding-in of the active ingredient.

The object is therefore achieved by a process for the preparation of directly compressible α-mannitol having a content of the α modification of greater than 90%, in which a) in a first step, an aqueous D-mannitol solution as starting material, spray gas, pulverulent α-mannitol and hot gas are combined, b) the resultant pulverulent product is precipitated into a fluidised bed, taken up, fluidised and transported further, and c) some of the pulverulent product formed is recycled into the process.

In a particular embodiment of the process, the resultant powder is, in one or more granulation step(s), sprayed with further liquid medium, dried and transported further in the fluidised bed.

For the preparation of the mannitol solution, use is made of D-mannitol having a purity of >90%, preferably >95%. Use is particularly preferably made of D-mannitol having a purity of >98%.

Surprisingly, the equilibrium can be shifted towards the formation of α-mannitol by recycling the α-mannitol formed as the dust fraction from the product discharge zone of the processor into step a) of the spray drying. In a particularly advantageous embodiment of the process, α-mannitol having a mean particle size of less than 20 μm, in particular having a mean particle size in the range from about 1 to 20 μm, preferably in the range from 3 to 15 μm, is recycled.

The recycling of the "dust-form" α-mannitol formed as pulverulent α-mannitol from the powder-metering device in line (9A) is effected by controlling the rotational speed of the star valve 10A via the fan (E) into the spray drying (step a).

After the equilibrium has been established, it is readily possible to recycle pulverulent α-mannitol having a mean particle size of less than 75 μm.

The particular design of the plant used enables the recycled pulverulent material to be comminuted, before the recycling, by grinding in the fan (E), which simultaneously serves as conveying element for the powder recycling.

Regulation of the rotational speeds of the star valves 10A and 10B of the plant used and grinding of the coarse (oversize) product formed to particle sizes of less than 75 μm in the fan (E) before recycling into the spray drying result in the exclusive formation of α-mannitol.

In order to carry out the process, an aqueous, at least >45%, preferably >50% D-mannitol solution is employed as starting material and is atomised at a temperature in the range from 60 to 95° C.

Air or an inert gas selected from the group consisting of $N_2$ and $CO_2$ can be used both as spray gas and as carrier and heating gas. The gas is preferably circulated in the process according to the invention, and the circulated gas is freed from particles by filters, dried in the condenser and fed back to the spray nozzles or heated and introduced into the fluidised bed.

The circulated gas is preferably freed from particles with the aid of dynamic filters.

In a particular embodiment of the process, the liquid media used have different compositions at different points of the plant.

Particle sizes of between 50 and 1000 μm can be produced specifically in the process according to the invention by varying the process parameters of spray pressure, spray amount, mannitol concentration, amount of powder recycled, hot-air stream and hot-air temperature.

For this purpose, the air fed to the plant is, in accordance with the invention, pre-heated to a temperature in the range 45–110° C. and the amount of feed air supplied is set in the range 1000–2000 $m^3/m^2$ per hour, giving a waste-air temperature of at least 40° C., preferably in the range 40–60° C. At the same time, the spray pressure of the two-component nozzles is set in the range 2–4 bar, so that from about 1.5 to 3 $m^3$/(h kg of solution) of hot gas are fed to the two-component nozzle, with the temperature of the hot gas being set in the range from about 80 to 110° C. Good process results are obtained if the powder recycling is regulated in such a way that recycling is carried out in an amount in the range 0.2–2.0 kg of solid/(h kg of solution).

Particularly uniform formation of pulverulent product having an α-mannitol content of >95% is carried out by adjustment of the parameters of spray pressure, amount of liquid, mannitol concentration, amount of powder recycled, hot-air stream and hot-air temperature, through which the amount of powder present in the fluidised bed is set to an amount in the range 50–150 $kg/m^2$ of bed.

Through experiments, a process has been found for the preparation of pure α-(D)-mannitol by means of which directly compressible mannitol (DC mannitol) having a suitable homogeneous particle size distribution can be prepared. The process is carried out using mannitol having a purity of greater than 98%, where the remainder can be sorbitol and other residual sugars. An aqueous solution having a mannitol content of about at least 45% by weight is prepared. Use is usually made of solutions having a mannitol content in the range 45–60% by weight. The solution prepared is atomised in a spray-drying plant at a feed-air temperature of about 60–110° C. and dried. For this process step, use is preferably made of an aqueous solution having a mannitol content of greater than 50% by weight. Through experiments, it has been found that the use of solutions comprising more than 60% by weight of mannitol is also possible under certain conditions and products having an α-mannitol content of >95% by weight are obtained The process is carried out using a plant as described in DE 1 99 27 537, but with a slight modification. By means of the plant described in this patent application, it is possible per se to vary the properties of spray-dried or granulated, pulverulent products as desired with respect to particle size, particle size distribution, moisture content and compressibility. However, the changes to the plant enable additional fine adjustment through the powder recycling.

In particular, the process is carried out in a spray-drying plant which comprises
 a) a spray-drying unit (B),
 b) a fluidised bed (A),
 c) one or more additional spray or atomisation nozzles for liquid media (C),
 e) a powder-metering device (D) and
 f) a powder recycling system (9) with fan (E), where the lines (9A) and (9B) intended for powder recycling are provided with star valves (10A, 10B), and the powder (8) which does not enter the powder-metering device can be separated into a dust-form fraction and a coarse fraction.

In the spray-drying unit (B) of the plant used in accordance with the invention, the liquid medium (5), spray gas (6), pulverulent material (9) and hot gas (4) are combined.

In a particular embodiment, a spray-drying unit (B) is located vertically above a subsequent horizontal fluidised bed in a spray tower.

In a particular embodiment, the spray-drying unit (B) of the plant can comprise a spray system which consists of a two-component spray nozzle heated by means of hot water with coaxially arranged powder recycling and surrounding hot-gas flow.

In the plant used, one or more additional spray or atomisation nozzles for liquid media (C) can be installed in the fluidised bed, also with variable location. The fluidised bed is followed by a powder-metering device (D), which is separated off by a valve flap (F) and which is fed by a product overflow (8). Some of the product formed can be recycled into the spray-drying unit (B) via fly conveying, in which a fan (E) serves as conveying element, if desired after comminution (9A, 10A) or without comminution (9B, 10B). The fan (E) acting as conveying element can simultaneously serve as comminution unit for the recycled powder.

In the process for the preparation of spray-dried pulverulent α-(D)-mannitol,
 a) in a first step, a liquid medium, spray gas, pulverulent material and hot air are combined,
 b) the existing pulverulent product is precipitated into a fluidised bed, taken up, fluidised and transported further, and, if desired,
 c) in one or more granulation step(s), sprayed with further liquid medium, dried
 d) and conveyed in the fluidised bed in the direction of the powder-metering device, from which
 e) some of the unground and/or ground, pulverulent material is recycled into the process.

The liquid medium is preferably a solution. However, it may also be an aqueous suspension of pre-formed α-(D)-mannitol, but this has to be atomised immediately after its preparation since α-(D)-mannitol is unstable in the presence of water and rearranges to the β form.

In a particular variant of the process, the recycled pulverulent material can be comminuted before the recycling.

The spray, carrier and heating gas used can be air or an inert gas selected from the group consisting of $N_2$ and $CO_2$. The gas can, in accordance with the invention, be circulated, it being freed from particles by filters or especially with the aid of dynamic filters, dried in the condenser and fed back to the spray nozzles or heated and introduced into the fluidised bed.

In order to carry out the process, the plant is initially charged with pulverulent starter material via the fill ports (3). A stream of air is produced in the spray-drying space via the chambers (1). The introduced starter material is fluidised by this stream of air and moves in the direction of the discharge flaps (F). The powder stream attains this direction of movement on generation of the air stream through a corresponding perforation of the Conidur plate. The fluidised product can be discharged by simply opening the valve flaps (F). At this point of the plant, devices are provided which enable the product to be recycled either into a powder-metering device or, via fly conveying, to the spray-drying unit. An overflow (8) for the finished product is located at the discharge above the powder-metering device. The fan (E) of the spray-drying unit serves both as conveying means for the product and as comminution unit for powder material to be recycled. Recycled powder material from the return line (9A, 9B) is combined with the corresponding media liquid (5), spray air (6) and hot air (4) through the particular design of the spray-drying nozzle. The corresponding powder or granular material is taken up by the fluidised bed and, as already described above, transported further. On passing through the granulation nozzles (C), further medium, which can have a different composition to that introduced into the spray nozzle with powder recycling, can be sprayed onto the particles formed. In this way, further granulation and re-setting of the particle size distribution can take place. The product from the chambers (1) is dried to the desired final moisture content by means of air introduced via the Conidur plates. Dynamic filters (G) integrated into the plant prevent discharge of powder particles into the environment.

Instead of the granulation nozzles (C), as shown in FIG. 1, one or more spray nozzles or spray-drying nozzles or alternatively only one, two or more than three granulation nozzles can be installed at the corresponding point of the plant. These additional nozzles may be located directly at the beginning of the fluidised bed or moved further to the back. The choice of site at which the powder material originally formed is re-sprayed one or more times is, inter alia, also dependent on the residual moisture content that the desired product is to have. It goes without saying that a product having a particularly low residual moisture content after the final spraying makes a longer residence time in the fluidised bed necessary than one having a higher residual moisture content.

As desired, different compositions can be applied through the various nozzles to the particle surfaces already formed, enabling particles having a layered structure to be obtained. However, it can also serve to achieve a more uniform particle size distribution.

It is furthermore possible to operate the plant not only with air as carrier medium. It is also possible to operate the entire plant in circulation with an inert gas, such as, for example, nitrogen or carbon dioxide.

The plant is designed in such a way that the parameters amount of liquid, spray pressure, amount of powder recycled, amount of hot gas, hot-gas temperature, amount of warm air, warm-air temperature, etc., can be regulated individually. The amount of powder recycled, the amount of liquid fed in and the spray pressure can therefore be set specifically depending on the desired properties with respect to moisture content, particle size and particle size distribution of the end product. As desired, pulverulent products having particle sizes of between 50 and 1000 $\mu$m can be produced in the plant described. Depending on the procedure and the process parameters selected, the particles can have a layered (onion) structure or an agglomerate structure.

The formation of the particles can be controlled particularly by a spray nozzle integrated into the plant, which is suitable for the production of spray-dried granules. This spray nozzle is a spray system (B) which consists of a two-component spray nozzle [(1), (2), (3)], which can be heated by means of hot water and which is in turn fitted with a powder recycling system (4) arranged around the two-component spray nozzle and a surrounding hot-gas flow (5). Specifically, the powder recycling system (4) can be arranged coaxially around the two-component spray nozzle.

The advantage of this spray system is that recycled powder comes into contact immediately at the exit of the two-component spray nozzle with the liquid droplets generated via the atomisation air. In order that the powder particles do not stick together and that the surface moisture can be drawn off, the spray and powder part of the spray nozzle with powder recycling is included in a hot-gas stream. Subsequent drying to the desired residual moisture content takes place in the fluidised bed.

In particular also through the incorporation of this spray-drying system, it is possible to produce certain particle sizes specifically.

A particular advantage of this spray-drying process therefore consists in that pulverulent $\alpha$-(D)-mannitol having very different properties with respect to moisture content, particle size, particle size distribution, bulk density and particle structure can be prepared in a single plant without further process steps for aftertreatment of the product depending on the process parameters set and on the liquid media to be atomised.

In order to obtain particularly good DC properties (DC=directly compressible) of the spray-dried substance, here $\alpha$-(D)-mannitol, it is advantageous to agglomerate the individual particles formed in the spray drying. For this purpose, a spray tower is located vertically above the fluidised bed above the spray-drying unit (B) according to the invention. In the depicted variant of the possible plant design, the fluidised bed is preferably constructed lying horizontally, in which the product is transported to the exit by the air stream that has been set.

The hot aqueous mannitol solution is atomised via one or more two-component nozzle(s) (5) (6), which is (are) heated with hot water (7). The spray jet produced is surrounded by a mannitol powder recycling system (9) arranged around this nozzle and a stream of hot gas (4). The solid crystallises in the spray jet, forms agglomerates and is taken up by the fluidised bed. Hot air from the air introduction chambers (1) flows through the fluidised bed and fluidises the latter. The base of the fluidised bed is a Conidur plate, which ensures specific transport of the solid in the direction of the discharge and also produces a defined residence time of the solid in the fluidised bed. The residence time of the product in the processor can furthermore be controlled via the bed depth, spray amount and recycle quantity. The solid is transported through a plurality of air introduction chambers (1) connected in series and dried to a residual moisture content of <0.3%. The drying operation takes place over the length of the fluidised bed in a certain temperature profile in order to prevent overheating of the product.

The water-laden and dust-containing fluidisation air is cleaned via dynamic filters (G) and discharged via the waste-air chambers (2). The dynamic filters are regularly cleaned by means of pulses of compressed air. The dust cleaned off binds the spray mist from the spray zone and prevents settling and baking of solid onto the walls.

The dried solid falls into a metering system for recycling (D) via double pendulum flaps (F) or other discharge systems. The discharged product can optionally be worked up further via a classification system. The oversize particles (and undersize particles) formed can be ground in the fan (E) above the powder recycling system (9) and recycled into the spray drier together with the undersize particles, i.e. with dust-form mannitol powder having particle sizes of less than 75 μm, in particular less than 40 μm.

A sub-stream is discharged as finished product (8) at the discharge. The product can be classified via a sieve, it being possible for the oversize particles (residual material or the coarse powder fraction) to be recycled via the suction side of the grinding fan (9A), ground and returned to the process. Inter alia, this minimises product losses.

The fan (E) of the spray-drying unit serves both as conveying means for product to be recycled (introduction of solid on the pressure side (9B)) and as comminution unit for recycled powder material (introduction of solid on the suction side (9A)). The two sub-streams of solid are controlled, for example, via the rotational speed of the star valves (10A, 10B). Recycled powder material from the return lines (9) is, as already described above, combined with the corresponding media liquid (mannitol solution) (5), spray air (6) and hot air (4) through the particular design of the spray-drying nozzle.

The feed air is fed to the fan (E) from the product discharge zone of the processor. In this way, the fine dust (<15 μm) is removed from the product at the same time (pneumatic classification). At the same time, the removal of this fine dust has the effect that greater tablet hardness values can be achieved on use of this product freed from fine dust.

In the case of sub-stream 9B, the option exists of screening the oversize particles (residual material) out of the recycling system after the star valve 10B in order to be able to control the process better. These oversize particles (residual material) can be introduced on the suction side into the grinding fan (E) or another comminution machine, ground and fed back to the process.

As already indicated above, the quality of the agglomerates and thus of the product can be controlled via the plant parameters, such as concentration, spray pressure, temperature, spray amount, amount of recycled powder, amount of principal air, dust extraction, bed depth, etc. A reduction in the height of the spray nozzle [(B)→(C)] above the fluidised bed enables the particle structure to be converted from an agglomerate (berry structure) into granules (onion structure). With the lowest possible arrangement of the nozzles (granulation nozzles (C)), the powder recycling (9) can take place via the fill ports (3). In order to obtain a directly compressible product continuously, both the particle structures and the modification, particle size distribution, water content, density, etc., must be monitored. It has been found that the best product for compression is obtained if mannitol is crystallised out in a fine needle structure.

Experiments have shown that it is necessary to maintain and monitor the set parameters of the spray-drying process in order to obtain pure α-mannitol which has constant, good compression properties.

In the preparation of a formulation, the DC α-mannitol is homogenised with the active ingredient in a mixer and can immediately be compressed to form a tablet. The intermediate steps of agglomeration or granulation with subsequent classification and drying are saved. The conversion of the α modification into the β modification can be controlled through the addition of water and the residence time. In the case of some active ingredients, this conversion has the advantage that they are bound into the grain structure of the mannitol.

In accordance with the invention, the starting material employed is preferably D-mannitol having a purity of >90%, particularly preferably having a purity of >95% and very particularly preferably having a purity of >98%. This starting material is employed in the form of an aqueous >40–50% solution and is atomised into the plant at a temperature in the range from 60 to 95° C. The solution is preferably heated to a temperature in the range from 70 to 95° C., in particular from 75 to 90° C., before the atomisation.

In accordance with the invention, solutions having different mannitol concentrations can be employed at different points of the plant. Thus, it has proven appropriate to charge spray nozzles above the fluidised bed in the direction of the product discharge with solutions having higher mannitol concentrations than spray nozzles located at the beginning of the fluidised bed. It is therefore possible to employ a solution having a mannitol concentration of about 60% by weight, based on the solution as a whole, at the end of the fluidised bed, whereas the two-component nozzle with powder recycling is preferably operated with an at least 45% by weight aqueous solution. In this way, the product properties can again be influenced in the desired sense, it being necessary to observe the plant parameters precisely in this procedure.

Through variation of the parameters spray pressure, amount of liquid, amount of powder recycled, hot-air stream and hot-air temperature, particle sizes of between 50 and 1000 μm can be set specifically.

It has furthermore been found that the parameters of the plant used in accordance with the invention have to be set as follows in order to obtain a uniform product:

The spray pressure of the two-component nozzles should be set in the range 2–4 bar, preferably in the range from 2.5 to 3.5 bar.

The amount of hot gas fed to the two-component nozzle should be regulated in such a way that from about 1.5 to 3 m$^3$/(h kg of solution) at a temperature of from about 80 to 110° C. are conveyed. It has been found that, with a relatively high feed of hot gas, better product quality is obtained if a relatively low temperature is used.

The powder recycling should be set in accordance with the invention in such a way that solids recycling takes place in the range 0.2–2.0 kg of solid/(h kg of solution), preferably in the range from 0.5 to 1.5 kg of solid/(h kg of solution). The process is particularly favourable if the solids recycling is in the range from 0.5 to 1.0 kg of solid/(h kg of solution).

In order to carry out the process, pre-heated air must be fed into the plant. Good results are achieved if the air fed to the plant is pre-heated to a temperature in the range 45–120° C. It is favourable for the process according to the invention if the feed air has a temperature in the range from 65 to 110° C. It is particularly advantageous for the formation of an α-mannitol powder having good compression properties if the temperature of the feed air fed in is in the range from 70 to 110° C.

The amount of feed air supplied should be regulated in accordance with the invention in such a way that 1000–2000 m$^3$/m$^2$ per hour, in particular from 1200 to 1700 m$^3$/m$^2$ per hour, are fed into the plant.

In combination with the other parameters set, favourable process conditions exist if the air stream is fed in the plant in such a way that the waste-air temperature is in the region above 40° C.

It has furthermore proven favourable to regulate the process conditions in such a way that the amount of powder located in the fluidised bed is set to an amount of 50–150 kg/m² of bed. It is particularly favourable if the amount of powder is in the range 80–120 kg/m² of bed.

It has also been found that the process can be controlled, in particular, by specific recycling of a powder having a selected particle size.

As can be seen from the plant diagram (FIG. 1), powder recycling can be carried out both by powder withdrawal from the fluidised bed and by recycling of a very finely divided powder fraction which is formed during finishing, i.e. during homogenisation of the particle size by screening and packaging of the resultant product.

It is also possible, prior to recycling, to comminute powders having relatively large particle cross sections in the fan (E) of the spray-drying unit. As already indicated above, the powder stream can be controlled by adjusting the rotational speed of the star valves (10A, 10B). In order to grind powder to be recycled to the desired particle size before the recycling, the rotational speed of the star valve 10A (B) should accordingly be set in such a way that recycling takes place via the fan with grinding.

Experiments have shown that the equilibrium can be shifted towards the formation of α-mannitol if the mean particle size of the recycled powder ground in the fan (E) is less than 75 µm. α-mannitol is particularly preferably formed if the mean particle size of the recycled powder is less than 40 µm. Surprisingly, it has been found that recycling of a powder having particle sizes of less than 20 µm gives mannitol powders having a proportion of the α-fraction of greater than 90%. It has particularly surprisingly been found that, in particular, recycling of the so-called dust fraction which is formed in the product discharge zone of the processor and is usually removed from the product results in a uniform product having a particularly high proportion of the α-fraction. The mean particle size of the dust fraction is in the range from about 1 to 20 µm, in particular in the range from 3 to 15 µm. In addition, it has been found that the dust from the recycling results in stable operation in the spray zone of the processor.

Since grinding in the fan (E) only gives these particle sizes with particular effort, the "dust-form" product fraction from the powder-metering device, which is formed in the plant in line (9A), is preferably recycled into the spray drying, in particular at the beginning of the process, by controlling the rotational speed of the star valve 10A by grinding. By simultaneously reducing the rotational speed of the star valve 10B, recycling of coarse mannitol fraction is reduced.

Surprisingly, it has been found that, after the equilibrium has been established in the direction of the formation of α-mannitol in a purity of greater than 95%, the process can be continued in a stable manner if the powder ground in the fan to a particle size of less than 75 µm is likewise recycled.

In this way, it is possible, surprisingly, to set the spray-drying process by exclusive recycling of the "dust fraction" formed by regulation of the rotational speeds of the star valves 10A and 10B at the beginning in such a way that only α-mannitol is formed. The relatively coarse fraction (the so-called oversize particles) of the mannitol powder formed can subsequently again also be recycled into the process without risking shifting the equilibrium. This has the advantage that adhesion of the particularly finely divided spray mist to the walls of the plant in long-term operation can be avoided and interruptions to the process can be prevented.

A suitable choice of the process parameters enables production of a product having a content of the α modification of greater than 90%. Constant monitoring of the product quality produced enables the fraction to be increased readily to a content of the α modification to greater than 95%.

In particular if the above-described plant parameters are set to the optimum and the other process parameters are monitored, the product obtained in the process according to the invention is a mannitol having the following properties:
directly compressible mannitol
purity of the α modification >95%
bulk density 350–500 g/l
residual moisture content <0.3%
particle distribution: $x_{50}$ at 200 µm: <10%<53 µm+<15%>500 µm
$x_{50}$ at 300 µm: <10%<100 µm+<10%>850 µm
$x_{50}$ at 450 µm: <5%<100 µm+<10%>850 µm Since the various modifications of the mannitol are very similar, they cannot be differentiated in the DSC on the basis of their melting points usually measured in analysis. Identification is only possible, for example, by means of X-ray or NIRS.

However, owing to the tablet hardness values achieved with the resultant product, significant differences from commercially available products are evident. Compared with a commercially available product which has a relatively high content of the α modification in the pulverulent mannitol, tablets having hardness values which are from about 45 to 70% higher are obtained with the α-mannitol prepared in accordance with the invention.

During storage of DC α-mannitol, it must be ensured that the atmosphere is dry. It is advantageous to carry out the storage of the DC α-mannitol in a WPC with PE bag and integrated desiccant, since the PE bag is not permeable to water vapour. Moisture converts the α modification of the mannitol into the β modification. Under the above-described conditions, storage of the DC α-mannitol for a number of years is possible.

Through experiments, it has furthermore been found that, compared with the δ form of mannitol, α-mannitol can be converted into the β form in a simple manner by addition of moisture. For this purpose, water is added in order to control the conversion of α-mannitol into β-mannitol through the addition and the residence time in this process step. It must be noted here that the mannitol particles may be modified if water is added in too great an amount and too quickly.

For homogeneous binding-in of active ingredients, the active ingredient is, in a first step after preparation of the directly compressible α-mannitol, introduced into a suitable mixer and homogenised with the α-mannitol.

In the preparation of a formulation, the DC α-mannitol is homogenised with the active ingredient in a mixer and can immediately be compressed to form a tablet. The conversion of the α modification into the β modification can be controlled through the addition of water and the residence time. In the case of some active ingredients, this conversion has the advantage that they are bound into the grain structure of the mannitol.

For better understanding and in order to illustrate the invention, a general flow chart (FIG. 1) of the spray-drying plant described is given below, along with examples which are within the scope of protection of the present invention.

FIG. 1 shows a generalised flow chart of a possible embodiment of a spray-drying plant employed for carrying out the process, in which the numbers and letters given have the following meanings:

| | |
|---|---|
| 1 | Air introduction chambers |
| 2 | Heating devices |
| 3 | Fill ports |
| 4 | Hot-air feed |
| 5 | Liquid feed |
| 6 | Spray air |
| 7 | Heating medium |
| 8 | Product |
| 9 | Powder |
| | (9A finely divided powder (dust), 9B coarse powder) |
| 10 | Star valve (10A and 10B) for regulating the powder recycling |
| A | Fluidised-bed apparatus |
| B | Spray-drying unit |
| C | Granulation nozzles |
| D | Powder-metering device |
| E | Fan for powder recycling |
| F | Valve flaps |
| G | Dynamic filter |

With reference to the components mentioned in the description and given in the flow chart, it is readily possible for the person skilled in the art to produce an appropriate plant for carrying out the process by selecting commercially available individual components. It goes without saying for the person skilled in the relevant art that both additional electrical and mechanical control units have to be installed for operation of the plant in order to be able to regulate and vary the parameters in the process according to the invention, as described.

For better understanding and in order to illustrate the invention, examples are given below of the preparation of directly compressible α-mannitol and of illustrative formulations in which the active ingredient is bound in the mannitol by conversion of the α modification into the β form. Both the examples and the flow chart are unsuitable for restricting the scope of protection of the present application to these alone, since it is readily possible for the person skilled in the art to carry out a very wide variety of variations in the design of the plant and to replace individual parts of the plant by devices having an equivalent action. It is also readily possible for him to carry out the given examples in a suitable manner in α modified form and likewise to achieve the desired result.

The following examples for the preparation of various DC β-mannitol grades serve to explain the present invention in greater detail.

EXAMPLES

Example 1

Preparation of a DC α-mannitol Having a Mean Particle Size $X_{50}$=200 μm

For preparation, the spray-drying plant is filled with about 70 kg/m² of α-mannitol as the bed. (This initially introduced bed should as far as possible have the desired product properties. If the bed material available should have other properties, the plant must be started up under gentle conditions until the equilibrium has shifted in the desired direction).

As fluidisation and feed air, the plant is operated with 1200 m³/m² h at a temperature of above 90° C. (Before start-up of the plant, it must be ensured that sufficient dust is present in the plant. Dust can be generated via the powder-metering device (D), the suction-side recycling system (9A) and metering device (10A) via the/with the fan (E) and blown into the plant). When sufficient dust is in the plant, the metering (10A) of the recycle is reduced, and the atomisation of mannitol solution is begun. The atomised solution has a concentration of about 45% and a temperature of about 75° C. At a spray pressure of about 3 bar (spray medium is air), about 45 kg/m² h of solution are atomised in the plant. About 0.5 kg of solid/(h kg of solution) is recycled into the spray zone via the recycling system (9, 10) via the powder-metering device (D). The star wheels (10A, 10B) are set in such a way that a sufficient amount of product (9A, 10A) is always ground in the fan (E) and conveyed back into the plant with the unground product (9B, 10B).

Evaporation of the water in the plant causes the formation of an equilibrium with a bed temperature of above 45° C. The waste-air temperature is above 40° C. (It must be ensured that the waste air is saturated as far as possible. This is advantageous for the efficiency of the process and for the mannitol crystallisation process). In this way, the best crystal structure and the purest α modification of the mannitol are obtained. Since the fan (E) takes its feed air from the product discharge zone before the valve flaps (F) of the plant (A), and the discharged product is thus dust-free due to the pneumatic classification, α-mannitol with excellent properties for direct compression is obtained at the product discharge (8). In order to obtain DC α-mannitol having the desired particle size distribution, it can be sieved after the discharge valve (F), i.e. before the product discharge (8) and the powder-metering device (D). It is advantageous for the process also to sieve the oversize particles out of the product to be recycled (9B, 10B), since they otherwise accumulate further in the spray zone and can cause problems in the fluidised bed. The undersize and oversize particles sieved out can be fed on the suction side to the fan (E), ground and fed back into the process together with the other recycled solids sub-streams (9A, 10A, 9B, 10B). In this way, product losses are minimised, and the process runs in a more stable manner through the additional dust recycling (ground product).

Example 2

Preparation of a DC α-mannitol Having a Mean Particle Size $X_{50}$=300 μm

As described in Example 1, the spray-drying plant is, for preparation, filled with about 100 kg/m² of α-mannitol as the bed and started up.

As fluidisation and feed air, the plant is operated with 1500 m³/m² h at a temperature of above 90° C. The mannitol solution to be atomised has a concentration of about 50% at a temperature of about 80–90° C. At a spray pressure of about 3 bar (spray medium is air), about 65 kg/m² h of solution is atomised in the plant. The star wheels (10A, 10B) are set in such a way that a sufficient amount of product (9A, 10A) is always ground in the fan (E) and conveyed back into the plant with the unground product (9B, 10B). Evaporation of the water in the plant causes the formation of an equilibrium with a bed temperature of about 45° C. The waste-air temperature is about 40–45° C. It must be ensured that the waste air is saturated as far as possible. The oversize particles from the product to be recycled (9B, 10B) are sieved out, since they otherwise accumulate further in the spray zone and cause problems in the fluidised bed. The undersize and oversize particles sieved out are fed on the suction side to the fan (E) and ground. They are fed back into the process together with the other recycled solids sub-streams (9A, 10A, 9B, 10B).

Example 3

Preparation of a DC α-mannitol Having a Mean Particle Size $X_{50}=450$ μm

As described in Example 1, the spray-drying plant is, for preparation, filled with about 120 kg/m² of α-mannitol as the bed. As fluidisation and feed air, the plant is operated with 1700 m³/m² h at a temperature of about 100° C.

The hot gas is fed to the spray zone in an amount in the order of about 1.6 m³/(h kg of solution) at a temperature of about 100° C. When all these parameters have been set, atomisation of mannitol solution can be begun.

The solution has a concentration of above 55% by weight at a temperature of about 90–100° C. At a spray pressure of about 3.5 bar (spray medium is air), about 100 kg/m² h of solution are atomised in the plant. Bed/product of about 0.8–1.0 kg of solid/(h kg of solution) is recycled into the spray zone via the powder-metering device (D) via the recycling system (9, 10). The star wheels (10A, 10B) are set in such a way that a sufficient amount of product (9A, 10A) is always ground in the fan (E) and conveyed back into the plant with the unground product (9B, 10B).

Evaporation of the water in the plant causes the formation of an equilibrium with a bed temperature of about 40–50° C. The waste-air temperature is about 40–45° C. It must be ensured that the waste air is saturated as far as possible.

The oversize particles from the product to be recycled (9B, 10B) are sieved out since they otherwise accumulate in the spray zone and cause problems in the fluidised bed. The undersize and oversize particles sieved out are fed on the suction side to the fan (E) and ground. They are fed back into the process together with the other recycled solids substreams (9A, 10A/9B, 10B).

The invention claimed is:

1. A process for preparing a directly compressible mannitol having a content of the α modification of greater than 90%, comprising:
    a) combining an aqueous D-mannitol solution, spray gas, pulverulent α-mannitol and hot gas with air or an inert gas of $N_2$ or $CO_2$ being used both as a spray gas and as a carrier and heating gas,
    b) precipitating the resultant pulverulent product into a fluidized bed, taking up, fluidizing and further transporting,
    c) recycling some of the pulverulent product formed into the process, and optionally
    d) spraying the resultant powder, in one or more granulation step(s), with a further liquid medium, drying and further transporting in the fluidized bed.

2. A process according to claim 1, wherein for preparing the mannitol solution employed, the D-mannitol has a purity of >90%.

3. A process according to claim 1, wherein for preparing the mannitol solution employed, the D-mannitol has a purity of >98%.

4. A process according to claim 1, wherein the α-mannitol formed as a dust fraction in a product discharge zone of a processor is recycled into a) of the spray drying, and the crystallization equilibrium is shifted towards the formation of α-mannitol.

5. A process according to claim 4, wherein the α-mannitol has a mean particle size of less than 20 μm.

6. A process according to claim 4, wherein the "dust-form" α-mannitol formed in a line is recycled into the spray drying from a powder-metering device as pulverulent α-mannitol by controlling a rotational speed of a star valve via a fan.

7. A process according to claim 1, further comprising, after the equilibrium has been established, recycling pulverulent α-mannitol having a mean particle size of less than 75 μm.

8. A process according to claim 1, further comprising, after the equilibrium has been established, recycling pulverulent unground α-mannitol.

9. A process according to claim 7, further comprising comminuting the recycled pulverulent material, before the recycling, by grinding in a fan, which simultaneously serves as a conveying element for the powder recycling.

10. A process according to claim 1, wherein regulating rotational speeds of star valves and a grinding of a coarse product formed to particle sizes of less than 75 μm in a fan before recycling into the spray drying results in the exclusive formation of α-mannitol.

11. A process according to claim 1, wherein an aqueous 45–60% D-mannitol solution is employed as a starting material and is atomized at a temperature of 60–95° C.

12. A process according to claim 1, further comprising circulation the gas, freeing the circulated gas from particles by filters, drying in the condenser and feeding back to the spray nozzles, or heating and introducing the gas into the fluidized bed.

13. A process according to claim 12, further comprising freeing the gas from particles with the aid of dynamic filters.

14. A process according to claim 1, wherein the liquid media have different compositions.

15. A process according to claim 1, further comprising varying a spray pressure, a spray amount, a mannitol concentration, an amount of powder recycled, a hot-air stream and a hot-air temperature to produce particle sizes of 50–1000 μm.

16. A process according to claim 15, further comprising pre-heating the air fed to the plant to a temperature in the range 45–120° C. and feeding an amount of feed air of 1000–2000 m³/m² per hour, to give a waste-air temperature in the region of above 40° C.

17. A process according to claim 15, further comprising setting the spray pressure of the two-component nozzles of 2–4 bar, and about 1.5–3 m³/h kg of solution of hot gas having a temperature of about 80–110° C. are fed to the two-component nozzle.

18. A process according to claim 15, wherein the powder recycling is conducted in an amount of 0.2–2.0 kg of solid/h kg of solution.

19. A process according to claim 15, further comprising adjusting the a spray pressure, an amount of liquid, a mannitol concentration, an amount of powder recycled, a hot-air stream and a hot-air temperature to set the amount of powder to 50–150 kg/m² in the fluidized bed.

20. A process according to claim 1, wherein the D-mannitol has a purity of >95% for preparing the employed mannitol solution.

* * * * *